United States Patent [19]

Estano

[11] Patent Number: 5,056,372
[45] Date of Patent: Oct. 15, 1991

[54] COPPER COLLET GRIP MECHANISM

[75] Inventor: Joseph S. Estano, Rockland, Mass.

[73] Assignee: GTE Laboratories Incorporated, Waltham, Mass.

[21] Appl. No.: 619,163

[22] Filed: Nov. 28, 1990

[51] Int. Cl.⁵ .............................................. G01N 3/04
[52] U.S. Cl. ......................................... 73/859; 279/28
[58] Field of Search ...................... 73/859; 279/28, 55, 279/32; 123/90.67

[56] References Cited

U.S. PATENT DOCUMENTS 4,080,824  3/1978  Starks ................................. 73/859
4,838,218  6/1989  Sato et al. ..................... 123/90.67 X Primary Examiner—Jerry W. Myracle
Attorney, Agent, or Firm—Carl F. Ruoff

[57] ABSTRACT

The present invention describes an improved collet grip for holding tensile bars during testing. The collet includes a 90° concave surface to match the machined tensile bar thereby improving the gripping action. The collet also has a taper on the inside diameter to compensate for any allowable taper in the machining process.

7 Claims, 3 Drawing Sheets

COPPER COLLET GRIP MECHANISM

BACKGROUND OF THE INVENTION

The present invention concerns grip mechanisms for testing tensile strength of materials. More specifically, an improved grip mechanism has been developed which reduces tensile bar failure at the buttonhead of the bar.

One method determining the usefulness of a ceramic material is by testing the ceramic material's tensile strength. In order to test tensile strength, the ceramic material is formed into a tensile bar and placed into a machine that provides a tensile force on the bar. The tensile force is measured at the point the bar ruptures. However, while testing tensile bars on an Instron Grip Assembly a high failure rate occurred at the buttonhead of the tensile bar. When this occurs the tensile strength measurement of the bar is not accurate. The present invention provides a grip mechanism for holding tensile bars that reduces the probability of buttonhead failure.

SUMMARY OF THE INVENTION

The present invention discloses a grip assembly having a plurality of members which form an annular channel. The channel has an entry end and an exit end with the entry end having a first surface substantially perpendicular to the axis of the channel and a transitional concave surface which joins the first surface. The concave surface travels in a 90° arc such that at an end of the arc the tangent of the concave surface is substantially parallel to the axis of the channel. There is a third annular surface parallel to the axis of the channel and joined to the end of the concave surface.

DETAILED DESCRIPTION OF PREFERRED EMBODIMENTS

One method of determining ceramic material strength is by measuring the tensile force required to pull apart the material. It is essential that the grip assemblies holding the tensile bar apply the force evenly around the buttonhead of the tensile bar. If there is uneven force applied about the buttonhead, the tensile bar will fracture at the buttonhead and give an inaccurate tensile strength measurement. The present invention provides a superior grip assembly for holding the tensile bar.

Figure 1:
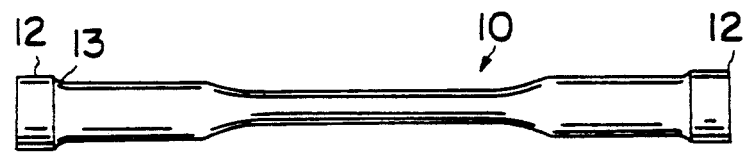
FIG. 1 shows a tensile bar suitable for tensile strength measurement.

FIG. 1 shows a tensile bar 10 suitable for testing. The tensile bar 10 has buttonheads 12 at each end. The tensile bar 10 has a gauge diameter of approximately 0.250 inch at the midpoint of the bar. The bar 10 tapers to approximately 0.472 inch diameter near the button heads 12. The buttonhead 12 tapers at point 13 which is where the bar 10 is held during the tensile strength measurement. The radius of curvature at 13 is approximately 0.120 inches.

Figure 2:
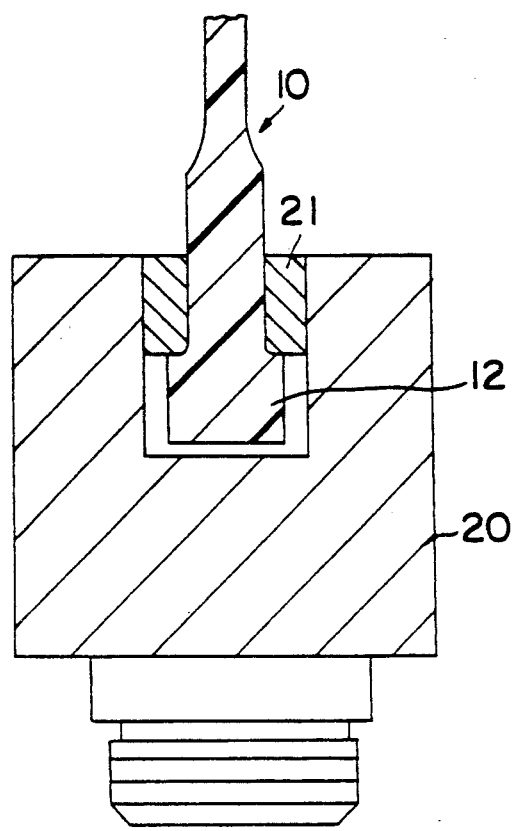
FIG. 2 shows a cross-sectional view of a grip assembly.

The current method for gripping for testing tensile strength of ceramic specimens is to hold the tensile bar in a grip assembly and measure the tensile force at the breaking point of the material. Copper collets are used in a grip assembly. Copper is the preferred material although other material can be used. A cross section of a grip assembly is shown in FIG. 2. The tensile bar 10 is held securely by the grip body 20 including the copper collet 21. The copper collet 21 holds the tensile bar at the buttonhead. The prior art grip contains a three section split copper collet, whose radius is approximately 30% smaller than that of the machined tensile bar and is designed with an 8 degree chamfer at the base as shown in FIG. 3(a-c).

Figure 3A:
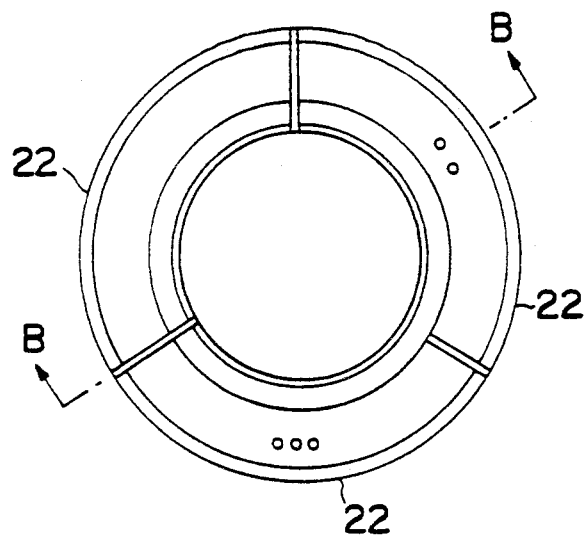
FIG. 3(a-c) shows various views of a prior art collet.
Figure 3B:
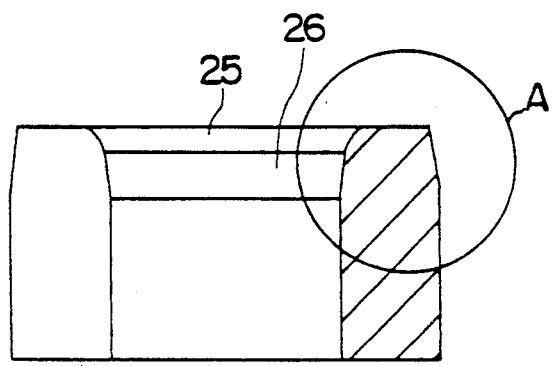
Figure 3C:
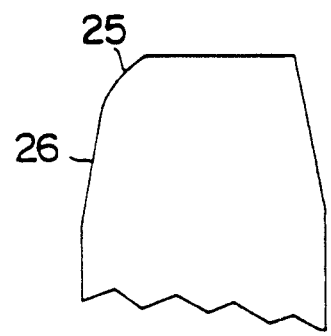
Figure 4:
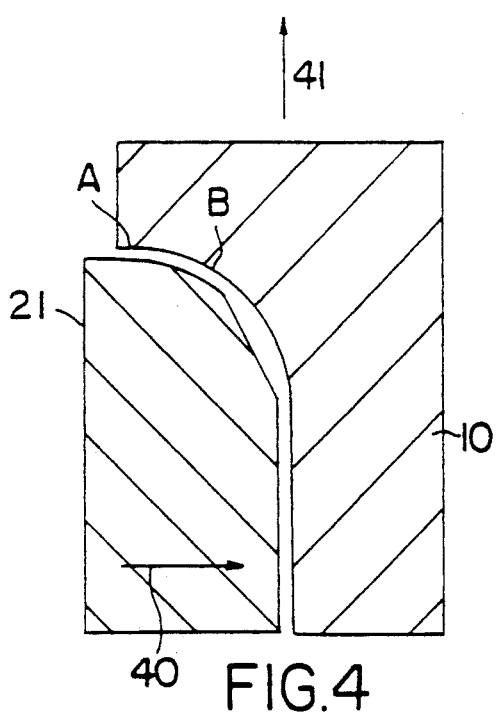
FIG. 4 shows the gripping action of the prior art collet.

FIG. 3(a) shows an overhead view of the copper collet used in the prior art. The collet 21 contains three pieces 22. FIG. 3(b) shows a view of the collet taken along line B—B of FIG. 3(a). FIG. 3(c) is a detailed view of area A in FIG. 3(b). FIG. 3(b) and 3(c) clearly shows that the collet of the prior art contains a rounded surface 25 which is then shaved off at 26. This surface 26 does not match the tensile bar and is therefore likely to cause an uneven distribution of force along the buttonhead of the tensile bar. As shown in FIG. 4 the prior art collet 21 of FIG. 3(a-c) produces a high contact angle which gives minimal advantage for developing radial or gripping forces as shown by arrow 40. The tensile force is shown by arrow 41. Thus, the contact of the collet 21 with the tensile bar 10 is only along the upper portion of the radius from point A to B. This can provide for uneven loading resulting in an increased probability of buttonhead failure.

Figure 6:
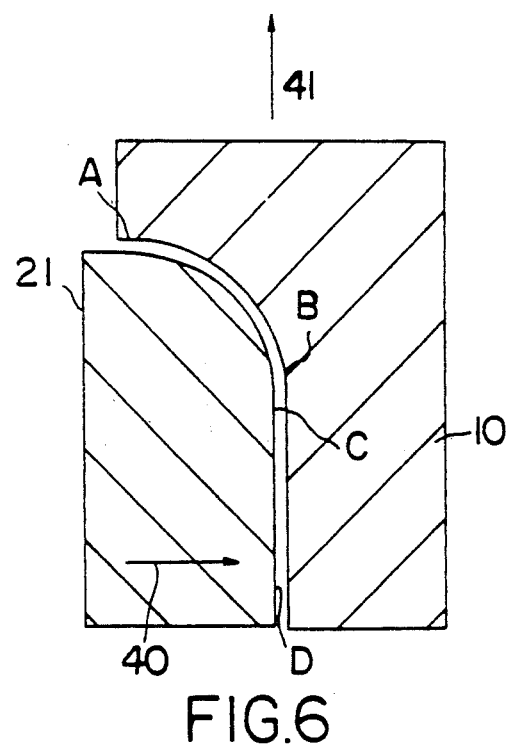
FIG. 6 shows the gripping action of the collet of the present invention.

The present invention provides a collet 21 which has two unique features and is shown in cross sectional view in FIG. 6. The first is the 90° spectrum of the 0.118 inch radius to match that of the tensile bar 10. This improves the maximum gripping effect that is achieved from the radial force 40 applied to the tensile bar 10. This force is arrived at through resolution of axial force 41 applied to the ceramic tensile bars and is equal to the axial force or tensile force divided by the tangent of the angle of the contact as depicted in FIG. 6. Thus, the lower the contact angle greater the mechanical advantage and gripping effect on the tensile bar. The collet 21 contacts the bar from point A to B. The second unique feature is a 0.0005 inch taper on the inside diameter of the collet as shown by arrows C and D. This feature compensates for any allowable taper common to the machine process used in the fabrication of the tensile bar.

Figure 5A:
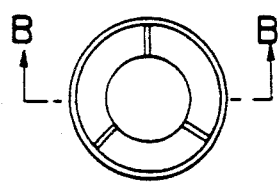
FIG. 5(a-c) shows various views of the collet of the present invention.
Figure 5B:
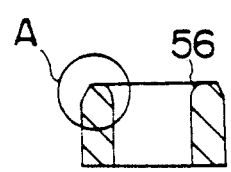
Figure 5C:
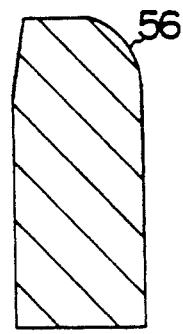

FIG. 5(a-c) shows the views of the improved collet of the present invention. FIG. 5(a) shows an overhead view of collet. FIG. 5(b) shows the view along line B—B of FIG. 5(a) and FIG. 5(c) shows a detailed view of the circle A in FIG. 5(b). As shown in FIG. 5(a-c) the collet has a smooth circular surface 56 which, as explained previously improves the loading on the tensile bar.

In the tests run to date using the improved copper collets of the present invention the buttonhead failure rate was reduced. Prior to using the improved collet of the present invention GTE Laboratories was experiencing a failure rate of 50-80% at the buttonhead of tensile bar. After use of the new collet there has been no record of a tensile bar failing at the buttonhead of a tensile bar.

While there has been shown and described what are at present considered the preferred embodiments of the invention, it will be obvious to those skilled in the art that various alterations and modifications may be made therein without departing from the scope of the invention.

What is claimed is:

1. A collet comprising:

a plurality of members forming an annular opening wherein each member has an upper surface, a transitional surface and an annular surface, the upper surface joining the transitional surface, the transitional surface being circular over a 90° spectrum and the transitional surface joining the annular surface, the annular opening being formed by the transitional surface and annular surface of each member.

2. The collet according to claim 1 wherein the annular surface tapers from the transitional surface so that the annular opening is larger at the point where the transitional surface and annular surface join than at any other point on the annular surface.

3. The collet according to claim 2 wherein the taper of the annular surface is at angle of 5 degrees with respect to the axial direction of the annular aperture.

4. The collet according to claim 1 wherein the number of members is three.

5. A grip assembly comprising a plurality of members forming an annular channel, the channel having an entry end and an exit end wherein the entry end has a cylindrical first surface substantially perpendicular to the axis of the channel and a transitional cylindrical concave surface, the concave surface joined to the first surface and traveling in a 90° arc such that at an end of the arc the tangent of the concave surface is substantially parallel to the axis of the channel and a third annular surface parallel to the axis of the channel and joined to the end of the concave surface.

6. The grip assembly according to claim 5 wherein the third annular surface tapers from the concave surface so that the annular channel cross-section is larger at the point where the concave surface and annular surface meet than at any other point along the annular surface.

7. The grip assembly according to claim 5 wherein the number of members is three.

* * * * *